United States Patent [19]

Olsson

[11] Patent Number: 5,415,996
[45] Date of Patent: May 16, 1995

[54] PROGNOSTIC MARKERS IN HUMAN BREAST CANCER

[76] Inventor: Lennart Olsson, 10 Katrina Ct., Orinda, Calif. 94563

[21] Appl. No.: 140,234

[22] Filed: Oct. 20, 1993

[51] Int. Cl.$^6$ .................. G01N 33/574; G01N 33/53; G01N 33/543
[52] U.S. Cl. .................................... 435/7.23; 435/7.9; 435/7.92; 435/7.94; 436/63; 436/64; 436/813; 424/1.49
[58] Field of Search ...................... 435/7.23, 7.9, 7.92, 435/7.94; 436/63, 64, 813; 424/9

[56] References Cited

U.S. PATENT DOCUMENTS 5,019,497  5/1991  Olsson ................................. 435/7.23

OTHER PUBLICATIONS

Martensson, S., et al., *Cancer Res*, vol. 48(8), pp. 2125–2131, Apr. 15, 1988.

*Primary Examiner*—Toni R. Scheiner
*Attorney, Agent, or Firm*—Bertram I. Rowland

[57] ABSTRACT

Methods and compositions are provided for determining the prognosis of human breast carcinoma through in vitro or in vivo detection of an antigen expressed and shed by cancer cells. The presence of this antigen is positively correlated with the presence of cancer and the number of cells expressing this antigen is correlated with a high incidence of tumor relapse, distant relapse and shortened relapse-free survival time.

29 Claims, No Drawings

PROGNOSTIC MARKERS IN HUMAN BREAST CANCER

The work disclosed herein was supported by a grant from the National Institutes of Health, grant number P50CA58187-02. The United States Government may have certain rights in this invention.

INTRODUCTION

TECHNICAL FIELD

The subject invention concerns the detection and treatment of cancerous cells of the breast.

BACKGROUND

Detection of breast carcinoma is classically determined by examination of a biopsy taken from a patient suspected of carrying such a tumor. These methods are inadequate not only because the patient is subjected to invasive, surgical techniques, but also because the information provided from such a method does not clearly indicate the prognosis of the patient from which the biopsy was taken. Prognosis concerns the likelihood that an individual may suffer occurrence, relapse or distant relapse of cancerous disease. Relapse is the recurrence of tumor growth due to propagation of tumor cells remaining in the host after surgery, new tumor cell development, or the like. Distant relapse concerns tumor dissemination such that tumor growth occurs at a site distant from the site of the original tumor. Of additional interest in the case of disease relapse is the length of the relapse-free survival time. Relapse-free survival time is the period between either surgical removal of the tumor or the suppression or mitigation of tumor growth and the recurrence of cancerous disease. Prognosis may be affected by various criteria such as histological type, tumor grade, tumor size, ploidy, and expression of certain hormone receptors such as estrogen receptor. These criteria provide some guidance in determining the need for and efficacy of subjecting the patient to various cancer therapies, such as irradiation, adjuvant therapy or surgical procedures such as mastectomy.

As an alternative to the more classical methods mentioned above, detection of cancer cell-associated products may find use in detecting the presence of breast carcinoma and in determining the prognosis of patients with breast cancer. Cancer cells synthesize unusual and sometimes highly specific glycolipids, glycoproteins and mucins. In many cases these proteins, glycolipids or mucins, which are produced as a result of aberrant gene expression, are presented on the surface of cancerous cells and may also be secreted or shed from the cell surface. Detection of these cancer-specific components may then serve as a marker for the presence of cancerous cells and also allow for determination of the prognosis of the host carrying the tumor.

RELEVANT LITERATURE

The identification, production and characterization of the monoclonal antibody 43-9F is described in Stranahan, et al. (1992) Cancer Res 52:2923–30, Mårtensson, et al. (1988) Cancer Res 48:2125–31, Pettijohn, et al. (1988) Proc Natl Acad Sci USA 85:802–6 Pettijohn, et al. (1987) Cancer Res 47:1161–69 and U.S. Pat. No. 5,109,497, issued May 28, 1991. The associations of 43-9F antibody reactivity and squamous lung cell carcinoma as well as human and embryonal testis carcinoma are described in Battifora, et al. (1992) Cancer 70:1867–72, Due, et al. (1987) Cancer Res 47:6697–6704, Miyake, et al. (1992) N Engl J Med 327:14–8, Giwercman, et al. (1990)Cancer65:1135–42 and Visfeldt, et al. (1992) APMIS 100:63–70. The association of H/Le$^y$/-Le$^b$ antigens and human non-small cell lung carcinomas is described in Miyake, et al. (1992) N Engl J Med327:-14–18.

Prognostic factors and treatment in axillary node-negative breast cancer patients are described in McGuire, et al. (1990) J Nat Cancer Inst 82:1006–25 and McGuire, et al. (1992) N Engl J Med 326:1756–61.

SUMMARY OF THE INVENTION

Methods and compositions are provided for the detection of the presence and amount of a carbohydrate antigen in samples from patients suspected of having breast carcinoma as diagnostic of the presence of such cancer. The antigens or antibodies may find use in vitro, as well as in diagnosis and therapy in vivo. Anti-idiotypic antibodies may also find use in the detection of the presence of antibodies in the blood or serum of a human host to the carbohydrate antigen.

DESCRIPTION OF SPECIFIC EMBODIMENTS

Compositions and methods are provided for detecting the presence of breast carcinoma in a human host by determining the presence of the carbohydrate sequence Gal$\beta$1-3[Fuc$\alpha$1-4]GlcNAc$\beta$1-4[Fuc$\alpha$1-3]GlcNAc$\beta$1-3Gal$\beta$1-4Glc (abbreviated Le$^a$-Le$^x$), a marker for breast carcinoma. The Le$^a$-Le$^x$ sequence is shared by a group of glycoproteins, in particular mucins, which are expressed on and shed from the surface of specific carcinoma cell types including squamous lung carcinoma (SLC), embryonal and human testis carcinoma and breast carcinoma cells. Other cancers, particularly epithelial-derived carcinomas such as prostrate cancer, bladder cancer, ovarian cancer, cervical cancer and the like, may also express the Le$^a$-Le$^x$ sequence.

The Le$^a$-Le$^x$ sequence may serve as a binding site for a variety of high molecular weight receptors which may be employed in the detection of Le$^a$-Le$^x$. These receptors include antibodies and fragments thereof, lectins, and the like with antibodies or fragments thereof being preferred receptors in diagnostic assays. Of significance to the operability of the subject invention is the ability of these receptors to distinguish the Le$^a$-Le$^x$ sequence from either Le$^a$ or Le$^x$ alone, as each Le$^a$ or Le$^x$ may be expressed independently on the surface of, and shed from, normal cells. In particular, antibodies should have very little or no cross-reactivity for Le$^a$ or Le$^x$ alone. Preferably the anti-Le$^a$-Le$^x$ antibodies should bind with higher affinity to Le$^a$-Le$^x$ than to Le$^a$ or Le$^x$ alone, with binding to Le$^a$-Le$^x$ at levels 500: 1, more preferably 1,000: 1, greater than binding to either Le$^a$ or Le$^x$ alone. Such a receptor, IgM monoclonal antibody 43-9F, secreted by hybridoma cell line ECACC No. 85013101 (deposited on Jan. 31, 1985 with the PHLS Centre for Applied Microbiology and Research, of the European Collection of Animal Cell Cultures (ECACC), Porton Down, Salisbury, Wiltshire, SP4 OJG, United Kingdom), was raised against a substantially purified glycoprotein fraction of SLC cells (U.S. Pat. No. 5,019,497, herein incorporated by reference). 43-9F has only little cross-reactivity to purified Le$^a$ and no cross-reactivity to either Le$^a$ or Le$^x$ as they are expressed on cells. Anti-Le$^a$-Le$^x$ antibodies which cross-react with 43-9F and thus specifically inhibit binding of 43-9F to $Le^a-Le^x$ are also of interest. In the absence of a receptor which is able to distinguish $Le^a-Le^x$ from either $Le^a$ or $Le^x$ alone, the subject method may be modified so that $Le^a$, $Le^x$ or cells expressing either $Le^a$ or $Le^x$ are substantially removed from the sample prior to analysis with the anti-$Le^a-Le^x$ receptor.

The breast cancer may be of several types including ductal, mucinous, lobular and the like, with ductal breast carcinoma being the most common. The cancer may be detected at any stage of tumor development, including hyperplasia, in situ and the like. The subject invention finds particular application for diagnosis where the human host carries an axillary lymph-node negative, ductal carcinoma of the breast, particularly where the host is classified as being low-risk. Low-risk patients are those having tumors less than or equal to 5 cm, axillary dissection without nodal metastases, localized tumor, (that is without invasion into skin or profound resection line), and having undergone radical operation. Radical operation is defined as an operation which the surgeon believes to have been successful in removing all tumor cells.

The $Le^a-Le^x$ sequence may be fucosylated or nonfucosylated and may be found on the surface of cells in biopsies from patients suspected of having breast carcinoma, in the blood of such patients, in lysates of tissue, transformed cells in culture or various cells associated with breast carcinoma. The antigen comprising $Le^a-Le^x$ may be part of a glycoprotein, mucin or polysaccharide substantially free of polypeptide. The level of expression of $Le^a-Le^x$ is directly associated with tumor cell proliferation in vitro as well as tumor cell, proliferation, progression and dissemination in animal models.

$Le^a-Le^x$ has also been shown to have value in the detection of human squamous lung carcinoma, as well as testis and embryonal testis carcinoma. The subject method may find particular application in patients having in situ carcinomas. Since detection of $Le^a-Le^x$ is indicative of the presence of a tumor which may disseminate, patients having in situ tumors may be placed under more careful observation than those patients having $Le^a-Le^x$ negative in situ carcinomas. The four known types of carcinoma associated with $Le^a-Le^x$ expression may be differentiated based on the type of patient to be examined. Where it is suspected or determined that a patient may have more than one type of carcinoma, classical methods of diagnosis, such as mammography, biopsy, and the like, may be employed to determine the specific site or organ responsible for $Le^a-Le^x$ expression.

In assays where the carbohydrate antigen is employed as a reagent, purified or substantially purified antigen may be obtained by a variety of techniques which are well known in the art. Furthermore, different forms of the antigen may be employed in assays, providing that the antigen is not adversely affected in its reactivity with receptors having binding specificity for the antigen. For example, carbohydrate chains comprising $Le^a-Le^x$ may be isolated by protease hydrolysis (e.g. protease K) of SLC cells, denaturation of the glycoproteins released, and elution of the chains by exclusion column chromatography in a molecular weight region corresponding to less than that of an ovalbumin marker (45 kDa). However, some portion of the carbohydrate composition elutes where exclusion is about 250 kDa. Digestion with endoglycosidase F, which cleaves both complex and high mannose type glycans near their asparagine attachment sites in glycoproteins, or with protease K results in the production of carbohydrate chains having about the same size. Endoglycosidase F digestion has no apparent effect on the antigenicity of the carbohydrate antigen. $Le^a-Le^x$ does not cross react with most tested blood group antigens as evidenced by direct and indirect agglutination and by dot-blot analysis on solubilized membrane preparations.

Antigens comprising $Le^a-Le^x$ may be isolated from $Le^a-Le^x$ positive cells (such as SLC cells or breast carcinoma cells) or from supernatant medium in which these cells are grown. The supernatant may be separated from the cells, insoluble material and cell debris removed (e.g., by centrifugation) and the glycoproteins precipitated at reduced temperature employing ammonium sulfate. The ammonium sulfate concentration is raised to about 75% w/v final concentration. The precipitates may be collected and further purified employing gel permeation columns, e.g., Sephacryl SX00 (X=2-4) columns. The bulk of the glycoproteins elute with the void volume, with S200, S300 and S400 columns. The equilibrating and eluting solution is conveniently phosphate buffered saline (PBS) plus a small amount of a non-ionic detergent (e.g., Tween 20) usually about 0.01 to 0.2%. Alternatively, the $Le^a-Le^x$ carbohydrate sequence or carbohydrates comprising the sequence may be produced synthetically using the methods described in Mårtensson, et al. (1988) *Cancer Res* 48:2125-31.

The isolated glycoprotein fraction or carbohydrate fraction may be used in accordance with conventional methods to immunize a mammal, (e.g., mouse or higher mammal, primate, or chimeric or transgenic animals which produce human immunoglobulins) in accordance with conventional procedures. See for example, EPO Pub. No. 0 044 722 and U.S. Pat. Nos. 4,172,124; 4,350,683; 4,361,549; and 4,464,465. Hybridomas may be prepared by fusing available myeloma lines, e.g., NS/1, Ag8.6.5.3, etc., with peripheral blood lymphocytes, splenocytes or other lymphocytes of the immunized host and the resulting immortalized B-lymphocytes (e.g., hybridomas, heteromyelomas, EBV transformed cells, etc.) selected, cloned and screened for binding to $Le^a-Le^x$. Alternatively, or in conjunction with such immortalization procedures, the genetic sequence encoding a specific $Le^a-Le^x$ binding region (i.e. antibody) or portion thereof may be cloned and expressed in bacteria, insect cells, mammalian cells or other cells.

Anti-$Le^a-Le^x$ monoclonal antibodies obtained and employed may be of any immunoglobulin class such as IgA, IgD, IgE, IgG and IgM, preferably IgG or IgM, and may be of any one of the subclasses of the classes. Whole antibodies, or fragments thereof which retain binding activity, may be employed, such as Fab, F(ab')$_2$, or the like. The subject immortalized B cells may be used as a source of DNA, either genomic or cDNA, for expression and/or modification of the light and heavy chains of the antibodies in prokaryotes or eukaryotes. The resulting product may then be used as receptors for binding to $Le^a-Le^x$.

Once the antibodies with binding specificity for $Le^a-Le^x$ are available, these antibodies may be used for screening. For example, by employing the monoclonal antibody 43-9F or antibodies against $Le^a-Le^x$ which are cross-reactive with the antibody 43-9F to $Le^a-Le^x$, one can rapidly screen for different antibodies, from the same or different host, which bind to $Le^a-Le^x$.

Anti-Le$^a$-Le$^x$ antibodies from a human host may be used as antigens for the production of monoclonal antibodies with binding specificity to the idiotypic site of the anti-Le$^a$-Le$^x$ antibodies. The anti-Le$^a$-Le$^x$ antibodies may be purified from serum of a human host carrying a carcinoma known to express Le$^a$-Le$^x$. Purification may be achieved by methods known in the art (e.g. binding of host antibodies to purified or synthetic Le$^a$-Le$^x$ in an affinity column, immunoprecipitation of antibodies with Le$^a$-Le$^x$ and the like). The purified human antibodies may then be employed as antigens in the production of monoclonal antibodies having binding specificity for the idiotype of the anti-Le$^a$-Le$^x$ antibodies. The anti-idiotypic antibody may be produced in any non-human host, e.g., rodent, more particularly, mouse. Techniques for the production of monoclonal antibodies are well known in the art. Of particular importance is that the anti-anti-Le$^a$-Le$^x$ monoclonal antibodies bind only to the idiotype of the host anti-Le$^a$-Le$^x$ antibodies and not to other portions of the antibody. Therefore, monoclonal antisera raised to human anti-Le$^a$-Le$^x$ antibodies must be screened and selected for the desired binding specificity. Anti-idiotypic antibodies may be used in diagnostic assays to detect anti-Le$^a$-Le$^x$ antibodies which may be present in a human physiological fluid (e.g., blood or serum) or in therapy. The presence of anti-Le$^a$-Le$^x$ antibodies in a sample from a host suspected of having breast carcinoma is indicative of expression of Le$^a$-Le$^x$ and thus the presence of breast carcinoma.

The presence of the Le$^a$-Le$^x$ antigen is directly correlated with the incidence of breast carcinoma and patient prognosis. Detection of the presence of Le$^a$-Le$^x$, and thus the presence of breast carcinoma cells, may be accomplished by employing immunohistochemical staining, dot-blot assays or the like, of tissue samples taken from patients suspected of having breast carcinoma. Alternatively, antigen comprising Le$^a$-Le$^x$ may be detected in acceptable physiologically-derived samples such as tissue lysates, blood-derived samples (i.e., blood, serum or plasma) or urine from such patients. Where a sample from a patient suspected of having breast carcinoma is found to contain Le$^a$-Le$^x$, the likelihood that the patient carries a breast carcinoma is substantially 80 to 90%. Patients having breast carcinomas which are Le$^a$-Le$^x$ negative have only a 20 to 30% likelihood of suffering relapse.

Of particular importance to the subject invention is the ability to quantitate the level of expression as determined by the number of cells associated with Le$^a$-Le$^x$. The number of cells expressing Le$^a$-Le$^x$ may then be correlated with patient prognosis. In one embodiment of the invention, the level of Le$^a$-Le$^x$ expression is determined as a percentage of cells in a biopsy which are found to express Le$^a$-Le$^x$ on the cell surface. Such expression may be detected by immunohistochemical assays, dot-blot assays, ELISA and the like. Where the patient samples have from a detectable amount of Le$^a$-Le$^x$ to <5% of the total number of cells expressing Le$^a$-Le$^x$, particularly >5% and <50%, more particularly >50% up to 100% being Le$^a$-Le$^x$ positive, the likelihood of tumor relapse is significantly high (from about 35 to 55% of the patients may be expected to suffer relapse compared to a relapse rate of 15 to 25% relapse rate of Le$^a$-Le$^x$ negative patients). Thus further or additional cancer therapy may be warranted.

Determination of the prognosis of patients having breast carcinoma is particularly facilitated where the two independent variables, expression of Le$^a$-Le$^x$ and tumor size, are considered. Where the patient is Le$^a$-Le$^x$ negative or has a tumor <1.5 cm in size, the likelihood of the occurrence of relapse is about 20-25%. In contrast, where a patient is Le$^a$-Le$^x$ positive and has a tumor >1.5 cm in size, the likelihood of relapse is about 50-55%. Distant relapse-free survival, which is defined as survival without formation of tumors distant from the original site, is also significantly inversely correlated with the combined analysis of the percent of Le$^a$-Le$^x$ positive tumor cells and tumor size.

Where tissue samples are employed, immunohistochemical staining may be used to determine the number of cells expressing Le$^a$-Le$^x$. For such staining, a multi-block of tissue is taken from the breast biopsy and subjected to proteolytic hydrolysis, employing such agents as protease K or pepsin. A normal human tissue sample may serve as a negative control while tissue known to express Le$^a$-Le$^x$ may serve as a positive control.

The tissue samples are fixed by treatment with a reagent such as formalin, gluteraldehyde, methanol, or the like. The samples are then incubated with a receptor, such as an antibody, preferably a monoclonal antibody, with binding specificity for Le$^a$-Le$^x$. This receptor may be conjugated to a label for subsequent detection of binding. Samples are incubated for a time sufficient for formation of complexes comprising Le$^a$-Le$^x$ antigen and antigen-specific receptor. Binding of the anti-Le$^a$-Le$^x$ receptor is then detected by virtue of a label conjugated to this receptor. Where the anti-Le$^a$-Le$^x$ receptor is unlabeled, a second labeled anti-receptor receptor may be employed. Examples of labels which may be employed include radionuclides, fluorescers, chemiluminescers, enzymes and the like.

Where enzymes are employed, the substrate for the enzyme may be added to the samples to provide a colored or fluorescent product. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

It is possible to select first receptor-specific compounds such that multiple labeled compounds bind each molecule of bound second receptor. Examples of such pairs include antibody/anti-antibody and avidin (or streptavidin)/biotin. Since the resultant signal is thus amplified, this technique may be advantageous where only a small amount of antigen is present. Samples determined to comprise Le$^a$-Le$^x$ are those samples for which the level of binding of the anti-Le$^a$-Le$^x$ antibody is significantly greater than the level of binding in negative controls and in the range of the level of binding in positive controls. The level of binding may then be correlated with levels of binding known to be associated with significantly increased relapse risk (i.e. the level of binding associated with expression of Le$^a$-Le$^x$ by at least 5% of cells). It is important that a significant number of cells in a section be examined, since tumors with only a small fraction of positive cells could otherwise be scored negative. A significant number of examined cells comprises at least all the cells contained within 3 to 6 fields of a tissue sample observed at a magnification of 100×. As the number of cells examined in a tissue sample increases, the confidence one may have in classifying a sample as Le$^a$-Le$^x$ negative increases.

The dot blot assay also may provide a high level of sensitivity in the detection of the presence and amount of $Le^a$–$Le^x$ in a blood-derived sample or a tissue sample taken from a host suspected of having breast carcinoma. The dot blot assay finds particular application where tissue samples are employed as it allows determination of the average amount of $Le^a$–$Le^x$ associated with a single cell by correlating the amount of $Le^a$–$Le^x$ in a cell-free extract produced from a predetermined number of cells.

To achieve this, a single-cell suspension is produced from tissue sample taken from a patient suspected of having breast carcinoma and the number of cells in each sample is determined. Tissues or cells which express $Le^a$–$Le^x$, preferably tissues or cells which express a known amount of $Le^a$–$Le^x$, may serve as a positive control and additionally may serve as a standard for comparison of results with test samples. Tissues or cells which lack $Le^a$–$Le^x$ may be employed as a negative control.

It is well known in the art that single-cell suspensions may be produced from tissue in a variety of ways (e.g. incubation with EDTA in PBS, trypsin digestion, etc.). The number of cells in each sample may be determined by various conventional means, e.g. by Trypan blue or eosin staining. Cell-free extracts may be prepared from the single-cell suspensions by extraction with a detergent, such as Triton X-100, sonication or other conventional means known in the art. To provide for precise quantitative results, the protein concentration of each cell-free extracts may be determined by methods known in the art and dilutions from each extract employed in the assay.

Each sample may than be bound to a soluble support, such as nitrocellulose or the well of a microtiter plate. Following washing to remove unbound material, areas of the support which are not bound to extract components may be blocked by incubation with a blocking agent such as PBS containing bovine serum albumin (BSA) to reduce non-specific binding of subsequent reagents to the support. The samples may then be washed and subsequently incubated with an anti-$Le^a$–$Le^x$ receptor, such as a monoclonal antibody, to allow for formation of complexes of $Le^a$–$Le^x$ and $Le^a$–$Le^x$-specific receptor. Binding of the receptor may be detected and analyzed as described above. Detection of $Le^a$–$Le^x$ in the test sample is indicative of the presence of breast carcinoma. The amount of complexes detected may be correlated with the number of cells in the original sample to determine the average amount of $Le^a$–$Le^x$ expressed per cell. The average amount of $Le^a$–$Le^x$ expressed per cell may then be compared to the average amount of $Le^a$–$Le^x$ expressed per cell in the positive control and standard samples and patient prognosis determined.

In an alternative embodiment of the invention, a blood or serum sample is taken from a host suspected of carrying breast carcinoma and the presence of $Le^a$–$Le^x$ determined. This determination may be performed using an antibody with binding specificity for antigen comprising $Le^a$–$Le^x$. Alternatively, the presence of $Le^a$–$Le^x$ may be determined indirectly employing an anti-idiotype antibody having binding specificity for anti-$Le^a$–$Le^x$ antibodies. Assays which may be employed for detection of antigen comprising $Le^a$–$Le^x$ include dot blot assays, ELISA, RIA, EIA, and the like. The soluble proteins may be separated from other cellular components and the crude extracts or substantially purified proteins then bound to a support, such as nitrocellulose or the well of a microliter plate. Blood samples taken from healthy individuals may serve as negative controls while samples known to contain $Le^a$–$Le^x$ may serve as positive controls. Following washing of the support to remove excess, unbound material, the samples are incubated with a blocking agent as described above. The samples are then incubated with a first receptor, such as an antibody, with binding specificity for either $Le^a$–$Le^x$. These receptors may be conjugated to a label for subsequent binding detection. Labels which may be employed are described above. Following formation of immune complexes, the samples are washed free of unbound material and the presence of the label conjugated to the receptor is detected. Where these first receptors are unlabeled, a second, labeled receptor specific for the first receptor may be incubated with the samples to allow formation of second complexes comprising first receptor, antigen and labeled second receptor. The presence of the label is then detected as described.

In another embodiment, purified, substantially purified or synthetically produced antigen comprising $Le^a$–$Le^x$ may be employed to determine the presence of $Le^a$–$Le^x$ in a host suspected of having breast cancer by virtue of the presence of host anti-$Le^a$–$Le^x$ antibodies. Antigen comprising $Le^a$–$Le^x$ may be bound to a support and the areas of the support lacking bound $Le^a$–$Le^x$ blocked as described above. A blood-derived sample from a patient suspected of having breast carcinoma may be incubated with the support-bound antigen, thereby allowing formation of complexes comprising support-bound $Le^a$–$Le^x$ and host anti-$Le^a$–$Le^x$ antibodies. A sample containing an antibody with known binding specificity for $Le^a$–$Le^x$ may be employed as a positive control while a sample containing an antibody with binding specificity for an antigen other than $Le^a$–$Le^x$ may be employed as a negative control. The samples are again washed and binding of the host anti-$Le^a$–$Le^x$ antibodies may be detected employing the methodology described above.

Another embodiment of the invention takes advantage of the fact that $Le^a$–$Le^x$ is associated with mucins of carcinoma cells. A sample from a patient suspected of having breast carcinoma may be combined with an antibody having binding specificity for the common core of the mucin proteins. The sample employed may be a cell-free extract prepared from patient tissue. Methods for preparing such extracts are described above. Alternatively, because mucins are shed from the cell surface and may be found in patient blood, blood-derived samples may also be employed.

Antibodies with binding specificity to mucins are commercially available or may be produced by methods known to those skilled in the art. Of particular importance is that the anti-mucin antibody employed have binding specificity to an epitope which is shared by all mucin proteins, for example an epitope found in the protein core of mucins. In addition, binding of the anti-mucin antibody must not inhibit access of subsequent antibodies with binding specificity for the $Le^a$–$Le^x$ carbohydrate sequence.

The patient sample and anti-mucin antibody are combined for a time sufficient for formation of first complexes of mucin and anti-mucin antibody. The immune complexes are then separated from the remainder of the sample to provide for a fraction substantially enriched for mucins. Separating may be achieved by immunoprecipitation techniques, centrifugation, affinity column chromatography and other techniques known to those skilled in the art. Alternatively separation of the complexes from the remainder of the sample may be achieved by binding the anti-mucin antibody to a support, such as nitrocellulose or the well of a microliter plate. Where a support is employed, a blocking step to reduce non-specific binding of subsequent reagents to areas of the sample devoid of antibody and/or washing steps to rid of excess reagents may be employed.

A second antibody with binding specificity for $Le^a$–$Le^x$ (e.g., 43-9F) is then combined with the first complexes to detect the presence of $Le^a$–$Le^x$ in the mucin bound to the first antibody. Samples known to contain $Le^a$–$Le^x$ may serve as positive controls while samples containing mucins which do not comprise the $Le^a$–$Le^x$ sequence may serve as negative controls. After formation of second complexes comprising anti-mucin antibody, mucin, $Le^a$–$Le^x$ and anti-$Le^a$–$Le^x$ antibody, excess material is washed away and binding of the anti-$Le^a$–$Le^x$ antibody is detected. Detection of anti-$Le^a$–$Le^x$ antibodies may be achieved by means of a label conjugated to the anti-$Le^a$–$Le^x$ antibody. Alternatively, a third labeled antibody with binding specificity for the anti-$Le^a$–$Le^x$ antibody may be employed. Labels which may be utilized have been described supra.

Where a third antibody is employed, it is of particular importance that the third antibody have binding specificity for the anti-$Le^a$–$Le^x$ antibody and no or very little binding to the anti-mucin antibody. This may be achieved by employing first and second antibodies which are produced in hosts of different species, with the third antibody having binding specificity for immunoglobulin from the host employed to produce the second antibody. For example, where the first antibody is produced in a goat and the second antibody is produced in a mouse, the third antibody may have anti-mouse immunoglobulin binding specificity. Alternatively, the third antibody may differentiate the first and second antibody by differences in the heavy chains of the antibodies. For example, where the first antibody is IgG and the second antibody is IgM, the third antibody may be anti-IgM.

The levels of binding of the anti-$Le^a$–$Le^x$ antibody (or third antibody having binding specificity for the anti-$Le^a$–$Le^x$ antibody) are then compared with the levels of binding in control samples. Where the levels of binding of the anti-$Le^a$–$Le^x$ antibody are significantly higher than binding of anti-$Le^a$–$Le^x$ antibody in the negative controls and is in the range of the level of binding in the positive controls, the sample comprises mucins having the $Le^a$–$Le^x$ sequence. The presence of $Le^a$–$Le^x$ is indicative of the presence of breast carcinoma in the patient from which the sample was originally derived.

Where a support is employed in assays for the detection of the presence of $Le^a$–$Le^x$, the support may be omitted and the reactions carried out in solution. This type of assay requires a means for separating uncomplexed reagents and reactants from complexes of reagents and reactants.

The subject invention may find use in in vivo imaging or therapy. Where in vivo imaging is employed, the patient may be injected, preferably by an intravenous route or at the suspected site of the tumor, with antibodies with binding specificity for $Le^a$–$Le^x$. The antibodies subsequently reach sites (i.e., by being transported through the bloodstream) where antigens comprising the carbohydrate sequence reside. Binding of the anti-$Le^a$–$Le^x$ antibodies may then be detected by virtue of a label, such as a radionuclide, e.g. technecium, rhenium, iodine, copper, indium, nmr additives, etc., conjugated to the antibodies. The label is detected by techniques known in the art such as radiography, nmr and the like. Detection of the label in tissues associated with the breast at a level higher than background levels (e.g., levels associated with cells which do not express $Le^a$–$Le^x$) is indicative of antibody binding and thus the presence of $Le^a$–$Le^x$ and carcinoma.

In vivo therapy of patients having a breast carcinoma expressing $Le^a$–$Le^x$ may be provided by injection (e.g., intravenous, intraperitoneal, etc.) of anti-$Le^a$–$Le^x$ anti-proliferative antibodies. Anti-$Le^a$–$Le^x$ anti-proliferative antibodies may include antibodies which inhibit tumor cell proliferation or facilitate tumor cell death by initiating or enhancing a host immune response against cells expressing $Le^a$–$Le^x$. For example, the anti-$Le^a$–$Le^x$ anti-proliferative antibodies may be of the IgM or IgG isotype and initiate complement activation upon binding the cell surface antigen or initiate antibody-dependent cell mediated cytoxicity (ADCC), thereby facilitating tumor cell death. Additional anti-$Le^a$–$Le^x$ anti-proliferative antibodies include anti-$Le^a$–$Le^x$ antibodies which are endocytosed after binding to cell surface $Le^a$–$Le^x$ antigen. When $Le^a$–$Le^x$ expressed on the surface of squamous lung carcinoma cells is bound to antibody, the antibody-antigen complex is endocytosed. As a result, the surface expression of $Le^a$–$Le^x$ is decreased on these cells. From these observations in squamous lung carcinoma cells one may expect that injection of the anti-$Le^a$–$Le^x$ antibodies may also result in decreased expression of $Le^a$–$Le^x$ on breast carcinoma cells. As a result, breast tumor growth or dissemination may be inhibited. In addition, the anti-$Le^a$–$Le^x$ anti-proliferative antibody may be conjugated to an anti-proliferative compound which may inhibit tumor cell growth as well as facilitate tumor cell death upon endocytosis. Examples of such compounds include radionuclides, toxins (such as ricin, diphtheria toxin, etc.) and the like. Thus anti-$Le^a$–$Le^x$ anti-proliferative antibodies, including unconjugated antibodies as well as antibodies conjugated to anti-proliferative compounds, may provide for in vivo cancer therapy which is specifically targeted to carcinoma cells expressing $Le^a$–$Le^x$.

The anti-$Le^a$–$Le^x$ antibodies or anti-idiotype antibodies specific for anti-$Le^a$–$Le^x$ antibodies may be administered by injection either by an intravenous, intraperitoneal, intramuscular or subcutaneous route, preferably an intravenous route. Where the antibodies are to be used for diagnosis of a known breast carcinoma, it may be preferable to inject the antibodies directly at the site of the suspected tumor. The antibodies may be administered for diagnosis or therapy in doses ranging from at least about 0.1 to 20 mg per kilogram body weight, normally from about 0.5 to 10 mg per kilogram body weight, preferably about 1 mg per kilogram body weight. The number of injections required for diagnosis will generally be at least 1. The number of injections required for therapy will generally range from at least 1 to about 10 generally at least about 4 injections. Injections may be administered over a period from at least about 1 month to 12 months, generally of at least about 3 months with administrations at intervals ranging from about 5 to 28 days, usually between 7 to 14 days, preferably about 10 days between injections.

The diagnostic methods of the subject invention may also be employed as follow-up to conventional therapies or in vivo therapies disclosed herein. Thus detection of Le$^a$-Le$^x$ and quantitation of the level of Le$^a$-Le$^x$ expression may be indicative of the effectiveness of current or previously employed cancer therapies as well as the effect of these therapies upon patient prognosis.

The following examples are offered by way of illustration and not by way of limitation.

EXPERIMENTAL

EXAMPLE I

METHODS

Patients.

In Denmark, breast cancer patients are followed in the Danish Breast Cancer Cooperative Group, which is a nation-wide surveillance and research program (West Andersen K, Mouridsen HT on behalf of Danish Breast Cancer Cooperative Group (DBCG). (1988) *Acta Oncologica* 27 Fasc. 6a: 627–47). According to this program, low-risk patients are defined as having tumors lesser than or equal to 5 cm, axillary dissection without nodal metastases, localized tumor (that is without invasion into skin or profound resection line), and having undergone radical operation. Radical operation is defined as an operation which the surgeon believes has been successful in removing all tumor cells. These patients had surgery only for the primary breast cancer without any adjuvant treatment.

For the present study, patients were selected for the purpose of obtaining a well defined group of low-risk patients with long follow-up. The population-based patient collection in this study ensures that the patient material is representative of a sample of women with low-risk breast carcinoma. To get minimal selection bias, an important criteria of inclusion in the study group was that patients must reside in 5 specific communes at Funen, Denmark, at the time of surgery. During the period Jan. 1, 1979 to Oct. 31, 1983, a total of 107 women with low-risk breast cancer living in the local area were submitted to Odense University Hospital. Only women were included, and none had previous malignant disease. Surgical methods employed did not affect the long-term survival time [Blicher-Toft, et al. (1992) *J Natl Cancer Inst Monogr* 11:19-25] and no patients receive adjuvant chemotherapy. The patient is thus accordingly consistent with the required criteria for a primary evaluation of a prognostic marker in node-negative breast cancer.

Surgical specimens were processed according to standard protocols and were fixed in formalin. Histological diagnoses were established reviewing the original paraffin embedded, hematoxylin and eosin stained slides. In three cases, the material could not be processed for technical reasons. Histologic classification (Sobin LH. (1981) International histological classification of tumors, no. 2: Histological typing of breast tumors, ed. 2 Geneva: World Health Organization, 15-25) of the remaining 104 cases revealed pure in situ lesions carcinoma in 6 cases, leaving 98 invasive carcinomas for further consideration. Eighty six of these were ductal, seven mucinous, and five lobular (Table 1). Only the 86 cases with common ductal carcinoma were included in the study. The surgical treatment consisted of total mastectomy with partial axillary dissection in 84 cases and breast conserving surgery with partial axillary dissection followed by irradiation in 2 cases. The patients were followed until Aug. 31, 1992. Even though patients were enrolled in DBCG, the medical records were revisited, especially for distant relapse and death of breast cancer.

Tumor Characteristics

Tumor size was measured by the pathologist as the largest tumor dimension. Anaplasia grading followed the criteria of WHO (Scarff, et al. (1968) Histological typing of breast tumors. International histological classification of tumors. WHO, Geneva. 19-20). Estrogen receptor expression was determined by the dextran coated charcoal assay as recommended by EORTC (EORTC Breast Cancer Cooperative Group (1980) *Eur J Cancer Clin Oncol* 16:1513-1515) and with modifications (Thorpe, SM. (1987) *Breast Cancer Res Treat* 9:175-189).

43-9F Antibody.

The generation and production of 43-9F monoclonal antibody has been described previously (Stranahan, et al. (1992) *Cancer Res* 52:2923-30 and U.S. Pat. No. 5,019,497). 43-9F has weak cross-reactivity (affinity about 1000-fold lower) to purified Le$^a$ (Mårtensson, et al. (1988) *Cancer Res* 48:2125-31 ), but with no detectable binding to Le$^a$ on cell surfaces (Pettijohn, et al. (1988) *Proc Natl Acad Sci USA* 85:802-6). Hybridoma culture supernatant containing 10–50 µg/ml 43-9F antibody was used throughout the study in a final dilution of 1:20.

Immunohistochemical Procedures and Interpretation of Slides

Using multiblocks with 15 different carcinomas, the reactivity of 43-9F antibody was analyzed with the labeled streptavidin-biotin technique (DAKO, Copenhagen, Denmark) which is well known in the art. The histochemical procedures employed were substantially those described by Pettijohn, et al. [(1987) *Cancer Res* 47:1161-69] with variation of the following conditions in pilot experiments: incubation times with antibody; ;pretreatment of sections with pepsin or protease K; 43-9F dilution; fixation time in formalin; visualization of the reaction with carbazole, 3,3-diamino benzidine (DAB), and DAB with nickel reinforcement. Optimal conditions were found to be pretreatment with pepsin (500 µg/ml) for 20 min, a final concentration of 43-9F at a 1:20 dilution (30–50 µg/ml antibody), incubation overnight with antibody, and development with carbazole. Variation of fixation time did not significantly affect the results. The modifications from earlier procedures improved the intensity of staining of some specimens, but did not change any specimen from negative to positive for 43-9F. Negative controls were included where the primary antibody was substituted with an irrelevant antibody of the same isotype. All slides were counter-stained with hematoxylin. Slides were interpreted and classified as either negative or as belonging to one of the following three groups according to the approximate fraction of carcinoma cells stained by 43-9F: 1) ≦5%, 2) >5% and ≦50% and 3) >50% and ≦100%. The slides were examined independently by two scientists.

Statistical Methods.

The variables associated with each tumor, including 43-9F staining pattern, patient age, maximum dimension of tumor, histological grade and for some tumors estrogen receptor were analyzed using Cox multivariate analysis [Cox (1972) *J Royal Stat Soc B* 34:187-220]. Those variable showing statistically significant association with relapse were further analyzed using the log-rank test [Zedeler (1988) Acta Oncologica 27 Fasc 6a:6-49-662] to test differences in both relapse free survival and survival among patient group that are either negative or having varying fractions of 43-9F positive cells.

RESULTS

Patients and Histological Classification.

Table 1 shows the main patient data. Median follow-up time is 10 years and 9 months (range 8 years, 10 months–13 years, 8 months), and the median age of patients at time of diagnosis is 59 years (range 33–86 years) with 16% being more than 70 years old. The median largest dimension of the tumors is 2 cm (range 0.3–5 cm). Estrogen receptor status was only evaluated in 38 cases. None of the patients had chemotherapy.

TABLE 1

Characteristics of Patients, Histological Classification and Grade, Age, and Staining with 43-9F Antibody.

| Patients | Median | Range |
|---|---|---|
| Age | 59 years | 33 to 86 years |
| Tumor size | 2 cm | 0.3 to 5 cm |
| Follow-up | 10 years, 9 months | 8 years, 10 months to 113 years, 8 months |

| Histologic type | All No. | % | 43-9F Expression No. | % |
|---|---|---|---|---|
| Ductal | 86 | (88) | 63 | 73 |
| Mucinous | 7 | (7) | 4 | 57 |
| Lobular | 5 | (5) | 4 | 80 |
| Total number | 98 | | 71 | 72 |

| AGE (YEARS) | 43-9F NEGATIVE | 43-9F POSITIVE | TOTAL | % POSITIVE |
|---|---|---|---|---|
| >30 and <=40 | 2 | 4 | 6 | 67 |
| >40 and <=50 | 5 | 12 | 17 | 71 |
| >50 and <=60 | 5 | 18 | 23 | 78 |
| >60 and <=70 | 9 | 17 | 26 | 65 |
| >70 and <=80 | 1 | 12 | 13 | 92 |
| >80 and <=90 | 1 | 0 | 1 | 0 |
| Total | 23 | 63 | 86 | 73 |
| TUMOR DIAMETER (CM) | | | | |
| 0.1 -<1=1 | 9 | 15 | 24 | 63 |
| 1.1 -<=2 | 8 | 28 | 36 | 78 |
| 2.1 -<=3 | 3 | 14 | 17 | 82 |
| 3.1 -<=4 | 2 | 4 | 6 | 67 |
| 4.1 -<=5 | 1 | 2 | 3 | 67 |
| Total | 23 | 63 | 86 | 73 |
| ESTROGEN RECEPTOR | | | | |
| Negative | 0 | 5 | 5 | 100 |
| Positive | 10 | 23 | 33 | 70 |
| Total | 10 | 28 | 38 | 74 |
| GRADE | | | | |
| Grade 1 | 9 | 21 | 30 | 70 |
| Grade 2 | 12 | 26 | 38 | 68 |
| Grade 3 | 2 | 16 | 18 | 89 |
| Total | 23 | 63 | 86 | 73 |

Staining Pattern of 43-9F Antibody in Breast Carcinomas. The 43-9F positive staining pattern is generally a distinct almost linear staining related to the cell surface membrane of the carcinoma cells. Even intracytoplasmic lumens were easily visualized in some 43-9F positive specimens. A granular, more or less cytoplasmic staining pattern could also be observed, dominating the pattern in some cases. However, this staining pattern was typically observed in single cells surrounded by otherwise typical, linearly stained cells. Nuclei were always 43-9F negative. The 43-9F staining was exclusively related to epithelial cells and all stromal and vascular components were completely 43-9F negative. Normal and hyperplastic benign glandular structures adjacent to tumor tissue sometimes stained with the 43-9F antibody. However, in those cases, the positive reaction was almost exclusively limited to the glycocalyx of the luminal part of the cells.

Among the 86 cases with ductal carcinoma, 63 (73%) contained 43-9F positive cells varying from all tumor cells being positive to only a few percent (Table 2). In the latter cases, the staining pattern was often focal with islets of 43-9F positive cells scattered around in otherwise negative tumor tissue. No relationship was observed between staining pattern and tumor necrosis or other histological findings. In situ carcinoma components also varied in the staining pattern from case to case.

TABLE 2

Number of Ductal Carcinoma Cases as Related to Distant Relapse, Death of Breast Cancer, and Per Cent of 43-9F Antibody Positive Cells.

| FRACTIONS OF CELLS STAINED WITH 43-9F | 43-9F STAINING OF PATIENT TUMOR | | DISTANT RELAPSE* | | NO RELAPSE* | | DEATH OF PATIENT* | |
|---|---|---|---|---|---|---|---|---|
| | NO. | % | NO. | % | NO. | % | NO. | % |
| Negative | 23 | (27) | 5 | (21) | 18 | (78) | 1 | (5) |
| <5% | 27 | (31) | 10 | (37) | 17 | (63) | 4 | (15) |
| >5% and <50% | 22 | (26) | 11 | (50) | 11 | (50) | 6 | (25) |
| >50% and ≤100% | 14 | (16) | 6 | (43) | 8 | (57) | 3 | (21) |
| Total number 43-9F Positive | 63 | (73) | 27 | (43) | 36 | (57) | 13 | (21) |
| Total number | 86 | | 32 | (37) | 54 | (63) | 14 | (16) |

*As observed over a median follow-up time of 10 years, 9 months.

The data were entered into a program for the stepwise fitting of Cox's proportional hazards regression model [Cox (1972) J Royal Stat Soc B 34:187–220]) with relapse as the outcome variable and five variables as potential independent predictors: 43-9F positive tumor cells, tumor size, patient age, tumor grade and anaplasia score. Only 43-9F positive tumor cells and tumor size were found to be significant predictors (P<0.05) of relapse. The presence of 43-9F positive tumor cells was more highly significant when used as a dichotomous (0,1) variable rather than as a continuous variable (0 indicates no staining, 1 indicates positive staining of any magnitude). These two variables, 43-9F staining and tumor size, are essentially independent of one another (Pearson's r=0.02, P=0.88; Spearman's $r_s$=0.07, P=0.52). The distribution of tumor sizes was similar for both relapse and non-relapse patients over the range 2.0 cm and 5.0 cm. Only 6 (19%) of the relapse patients had tumors smaller than 1.6 cm, whereas 26 (48%) non-relapsing patients had tumors in that size range. Dichotomizing both variables, as shown in Table 3, illustrates the joint predictability achievable with these two measures.

TABLE 3

Correlation Between Distant Relapse and Combined 43-9F Staining plus Tumor Size

| 43-9F STAINING* AND TUMOR SIZE | OCCURRENCE OF RELAPSE + | − | TOTAL | % POSITIVE |
|---|---|---|---|---|
| Negative or <1.5 cm | 10 | 34 | 44 | 23 |
| Positive and >1.5 cm | 22 | 20 | 42 | 52 |
| Total | 32 | 54 | 86 | |

*Samples containing any cells which bind 43-9F are classified as 43-9F positive.

The analysis using the log-rank test indicates that there is a prognostic relationship between relapse-free survival time (i.e., the period between cancer surgery and the occurrence or recurrence of tumor growth) and 43-9F positive tumor cells as well as tumor size. Both have $P<0.05$. Within a period of three years after diagnosis, 30–40% of patients having 43-9F positive tumors or having a tumor greater than 1.5 cm in size suffer relapse. In contrast, only about 10% of the patients with 43-9F negative tumors or having a tumor less than 1.5 cm in size suffer relapse within this same time period. While the most cases of relapse occur within the first 2 to 3 years after surgery, relapse may occur at any time after disease. However, in this study the incidence of relapse dropped significantly at 8 to 9 years after diagnosis.

Combining the variables shows that patients having both 43-9F positive cells and a tumor >15 mm in size had even shorter relapse-free survival time ($P<0.002$) than patients having either indicator alone. Within 2 to 3 years after diagnosis, approximately 45% of patients having both 43-9F positive tumor cells and a tumor greater than 1.5 cm in size suffered relapse. Within 8 years after diagnosis, approximately 50% of these patients suffered relapse. Further, a significant correlation was found between distant relapse-free survival time and the percentage of tumor cells staining positive for 43-9F. The higher the percentage of tumor cells staining positively with 43-9F, the shorter the distant relapse-free survival time experienced by the patient ($r=0.309$, $t=1.77$, $P<0.05$). For example, patients having tumors with approximately 30% 43-9F positive cells are most likely to suffer relapse within two years, while patients having only 10% or less 43-9F positive tumor cells may be free of relapse for a period of 8 years or more. No significant relationship was observed between staining pattern with 43-9F and age of patients, estrogen receptor expression and anaplasia grading (Table 1). Also, estrogen receptor expression had no significant relationship to relapse-free survival time.

The sensitivity (probability of a patient having $Le^a$–$Le^x$ being among those patients who subsequently relapse) and specificity (probability of patient not having $Le^a$–$Le^x$ being among those patients who do not subsequently relapse) of predicting distant disease relapse employing the indicators of 43-9F staining and tumor size, either alone or in combination, are shown in Table 4. As single predictors, 43-9F staining and tumor size each have a sensitivity in the range of 80–85%. However the specificity of the 43-9F staining variable is 33% while the specificity of the tumor size variable is 48%. Among the 32 patients who relapsed, only one patient had both a 43-9F negative tumor which was less than 1.5 cm in size. Therefore, if one employed 43-9F staining or tumor size as a predictor for no relapse, the sensitivity is 97%, but the specificity is reduced to 19%. One would therefore indicate a false positive prediction of disease relapse for 81% of those patients who are destined not to relapse. In contrast, the data for predicting relapse for patients with tumors that are 43-9F positive and larger then 1.5 cm has a sensitivity of 69% and a specificity of 63%. Therefore, these results again show that 43-9F staining is a useful indicator of the incidence of distant relapse, particularly when the tumor size is also considered.

TABLE 4

Sensitivity and Specificity of Predicting Distant Disease Relapse as Related to 43-9F Staining Pattern and Tumor Size.

| Indicator | Sensitivity (%) | Specificity (%) |
|---|---|---|
| 43-9F positive staining alone | 84 | 33 |
| Tumor size >1.5 cm | 81 | 48 |
| Tumor positive for 43-9F or tumor size >1.5 cm | 97 | 19 |
| Tumor positive for 43-9F and tumor size >1.5 cm | 69 | 63 |

EXAMPLE II

The presence of breast carcinoma in a patient is determined through detection of the presence of antigens comprising $Le^a$–$Le^x$ in a blood sample from the patient. A sample of at least 1 ml is taken from the patient. A blood sample from a patient free from cancer serves as a negative control while a sample containing glycoproteins comprising $Le^a$–$Le^x$ serves as a positive control. The blood samples are subjected to separation techniques or are used undiluted. Where an enzyme-linked immunosorbent assay (ELISA) is employed, wells of a microtiter plate are coated with the blood sample. The wells are washed free of excess or unbound material and the areas of the support which subsequently do not contain bound material are blocked by incubation with a blocking reagent such as 5% bovine serum albumin (BSA) in phosphate-buffered saline (PBS). After a second washing step, the monoclonal IgM antibody 43-9F is then added to each well at a final concentration of 100 ng/well. The samples are incubated for 1 hr at 20° C. and again for 1 hr at 37° C. The wells are washed with PBS containing 0.1% Tween and then incubated with a peroxidase-conjugated secondary antibody with binding specificity for the 43-9F antibody (e.g., a goat anti-mouse IgM antibody). The samples are washed with PBS containing Tween and are incubated with substrate as described by Kennett (1980) in: Monoclonal Antibodies, Kennett, et al., eds., Plenum Press, NY, pg. 376–377. The optical density (OD) of each sample is then determined using a microliter plate scanner. Those test samples having an antigen comprising $Le^a$–$Le^x$ are those samples which have an OD in the range of the OD values of the positive control samples and significantly higher than that of the negative control samples.

EXAMPLE III

The presence of breast carcinoma is determined by detecting the presence of $Le^a$–$Le^x$ on mucins associated with breast tissue. The patient prognosis is determined by taking into account both the tumor size and the presence of $Le^a$–$Le^x$. Breast tumor size is determined by conventional means. A single cell suspension is prepared from a sample of the breast tumor by incubation with 10 mM EDTA in PBS for 10–15 rain at 37° C. The sample is then pipetted to break up clumps. The number of cells in the sample may be determined by counting a diluted sample in a hemacytometer. Cell viability is determined by eosin staining.

A cell-free extract is prepared by extracting the single-cell suspension with 1.0% Triton X-100 detergent on ice for 10 min. The sample is then centrifuged to separate the supernatant containing the soluble protein fraction from the insoluble cell debris. The supernatant is placed in the well of a microtiter plate having goat anti-mucin antibody pre-bound to the surface. Areas of the well lacking the anti-mucin antibody have been previously blocked by incubation with BSA. Concurrently a sample containing mucin which does not comprise the Le$^a$-Le$^x$ sequence and a sample containing mucin which comprises Le$^a$-Le$^x$ are added to separate wells to serve as negative and positive controls, respectively.

The sample is incubated for 1 hr at 20° C. and again for 1 hr at 37° C. The samples are then washed with PBS to remove unbound material and then incubated with the murine IgM monoclonal antibody 43-9F for 1 hr at 20° C. and for an additional hour at 37° C. After washing with PBS, a third anti-murine IgM antibody conjugated to peroxidase is incubated with the samples. The samples are washed with PBS and incubated with substrate as described in Example II. The OD of each sample is determined and the values for test, positive and negative controls compared. Those test samples which have values significantly greater than that of the negative control and in the range of values for the positive control comprise Le$^a$-Le$^x$. The presence of Le$^a$-Le$^x$ correlates with a 80–90% likelihood that a breast carcinoma is present in the patient. The independent variable of Le$^a$-Le$^x$ expression and tumor size are then considered in determining the prognosis. Where the cell-free extract is determined to contain Le$^a$-Le$^x$ and the tumor size is greater than 1.5 cm, the likelihood of the patient suffering relapse is approximately 50%. Where the sample is Le$^a$-Le$^x$ negative or the tumor size is less than 1.5 cm, the likelihood of patient relapse is approximately 25%.

The decision as to whether to employ cancer therapy, such as adjuvant therapy, surgery, or post-surgical adjuvant therapy, is complicated by the lack of methods which clearly indicate which patients are at significant risk of occurrence or relapse of disease. Ideally, adjuvant therapy should be limited to those patients who are at such significant risk. The subject invention provides a method to indicate which patients having, or suspected of having, breast carcinoma are at a high risk of disease occurrence or relapse and which are at low risk. It is evident from the above results that the level of expression of Le$^a$-Le$^x$ is indicative of the presence of breast carcinoma and is also positively correlated with a high risk of disease relapse as well as with shortened relapse-free survival time. In addition, combining the variable of Le$^a$-Le$^x$ expression and tumor size allows for determination of prognosis with even greater confidence.

The antigens comprising Le$^a$-Le$^x$ are mucins, glycoproteins, or fragments thereof, and may be employed by themselves or in conjunction with complementary receptors, such as antibodies, as reagents in diagnostic assays. Antibodies having binding specificity for Le$^a$-Le$^x$ can be used in cytology of biopsies for the detection of the presence of antigens comprising Le$^a$-Le$^x$. Of particular interest is the ability to detect the presence of antigens comprising Le$^a$-Le$^x$ or the presence of anti-Le$^a$-Le$^x$ antibodies in patient blood or serum. This latter method provides a non-invasive technique for determining the presence of breast carcinoma and for evaluating the need for and efficacy of available breast cancer therapies. In addition, anti-Le$^a$-Le$^x$ antibodies, or anti-idiotype antibodies with binding specificity to anti-Le$^a$-Le$^x$ antibodies, may be employed in in vivo imaging and therapy. Such techniques may allow detection of breast carcinoma at an early stage of tumor development as well as determination of the precise location of the tumor in the human host. The subject invention may also be employed in detecting the post-therapeutic recurrence of tumor growth by detecting the presence of either Le$^a$-Le$^x$ or anti-Le$^a$-Le$^x$ antibodies. Furthermore, in vivo imaging may allow for detection of metastases from the breast carcinoma as distinct from the original tumor. The subject method allows for the instigation of aggressive, often drastic treatments only where it is determined that a tumor is present and/or that the likelihood of the occurrence of serious cancerous disease or relapse of disease is high.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of screening for the presence of breast carcinoma in a human host suspected of having breast carcinoma, said method comprising the steps of:
   combining a sample from said human host with monoclonal antibodies which specifically bind the carbohydrate Gal$\beta$1-3[Fuc$\alpha$1-4]GlcNAc$\beta$1-4[Fuc$\alpha$1-3]GlcNAc$\beta$1-3gal$\beta$1-4Glc; and
   detecting the presence of immune complexes;
   wherein, the presence of said immune complexes is indicative of the presence of breast carcinoma in said host.

2. A method according to claim 1, wherein said monoclonal antibody is IgM monoclonal antibody designated 43-9F secreted by hybridoma cell line having deposit number ECACC 85013101 or an antibody which specifically binds the epitope specifically bound by the monoclonal antibody designated 43-9F.

3. A method according to claim 1, wherein said sample is tissue.

4. A method according to claim 1, wherein said sample is a blood-derived sample.

5. A method according to claim 1, wherein the monoclonal antibodies are labeled with a detectable label.

6. A method according to claim 1, wherein said detecting is achieved by detection of binding of a labeled antibody having binding specificity for the monoclonal antibodies.

7. A method for evaluating the prognosis of a human host suspected of having breast carcinoma, said method comprising the steps of:
   combining a sample from said human host with monoclonal antibodies which specifically bind the carbohydrate Gal$\beta$1-3[Fuc$\alpha$1-4]GlcNAc$\beta$1-4[Fuc$\alpha$1-3]GlcNAc$\beta$1-3Gal$\beta$1-4Glc; and detecting the amount of immune complexes;
wherein, the amount of said immune complexes in indicative of the prognosis of said host.

8. A method according to claim 7, wherein said monoclonal antibody is IgM monoclonal antibody designated 43-9F secreted by hybridoma cell line having deposit number ECACC 85013101 or an antibody which specifically binds the epitope specifically bound by the monoclonal antibody designated 43-9F.

9. A method according to claim 7, wherein said sample is tissue.

10. A method according to claim 7, wherein said sample is a blood-derived sample.

11. A method according to claim 7, wherein the monoclonal antibodies are labeled with a detectable label.

12. A method according to claim 7, wherein said detecting is achieved by detection of binding of a labeled antibody having binding specificity for the monoclonal antibodies.

13. A method for evaluating the prognosis of a human host suspected of having breast carcinoma, said method comprising the steps of:
combining a blood-derived sample from said human host having breast carcinoma with a first antibody which specifically binds the carbohydrate Gal$\beta$1-3[Fuc$\alpha$1-4]GlcNAc$\beta$1-4[Fuc$\alpha$1-3]GlcNAc$\beta$1-3Gal$\beta$1-4Glc, said combining being for a time sufficient for formation of first complexes comprising said carbohydrate and said monoclonal antibody;
combining said first complexes with a second antibody conjugated to a label capable of providing a detectable signal, wherein said second antibody specifically binds said first antibody, for a time sufficient for binding of said second antibody to said first antibody; and
determining an amount of said label present on bound second antibody;
wherein, said amount is indicative of the presence of breast carcinoma in said host and correlates with the prognosis of said host.

14. A method according to claim 13, wherein said label is an enzyme, radionuclide or fluorescer.

15. A method for evaluating the prognosis of a human host suspected of having breast carcinoma, said method comprising the steps of:
combining a breast tissue sample from said human host with monoclonal antibodies which specifically bind the carbohydrate Gal$\beta$1-3[Fuc$\alpha$1-4]GlcNAc$\beta$1-4[Fuc$\alpha$1-3]GlcNAc$\beta$1-3Gal$\beta$1-4Glc for a time sufficient for formation of immune complexes; and
determining the number of cells in said breast tissue sample associated with immune complexes;
wherein, the number of cells in said breast tissue sample associated with immune complexes is indicative of the prognosis of said host.

16. A method of screening for the presence of breast carcinoma in a human host suspected of having breast carcinoma, said method comprising the steps of:
producing a cell-free extract from a breast tissue sample from said host;
combining said cell-free extract with antibodies which specifically bind the carbohydrate Gal$\beta$1-3[Fuc$\alpha$1-4GlcNAc$\beta$1-4[Fuc$\alpha$1-3]GlcNAc$\beta$1-3Gal$\beta$1-4Glc; and
detecting the presence of immune complexes in said sample;
wherein, the presence of said immune complexes is indicative of the presence of breast carcinoma in said host.

17. A method of screening for the presence of breast carcinoma in a human host suspected of having breast carcinoma, said method comprising the steps of:
combining a sample from said host with a first antibody which specifically binds an epitope of mucin, said epitope being common to all mucins, for a time sufficient for formation of first complexes comprising mucin and first antibody, said formation of first complexes providing for a fraction substantially enriched for said mucins;
combining said first complexes with a second antibody which specifically binds the carbohydrate Gal$\beta$1-3[Fuc$\alpha$1-4]GlcNAc$\beta$1-4[Fuc$\alpha$1-3]GlcNAc$\beta$1-3Gal$\beta$1-4Glc, said combining being for a time sufficient for formation of second complexes comprising first antibody, mucin, second antibody and said carbohydrate; and
detecting the presence of said second complexes;
wherein, the presence of said second complexes indicates the presence of said carbohydrate and is indicative of the presence of breast carcinoma.

18. A method according to claim 17, wherein said detecting is by means of a label conjugated to said second antibody, said label providing a detectable signal.

19. A method according to claim 17, wherein said detecting is achieved by detection of binding of a labeled antibody which specifically binds said second antibody.

20. A method of screening for the presence of breast carcinoma in a human host suspected of having breast carcinoma, said method comprising the steps of:
injecting into said host an antibody which specifically binds the carbohydrate Gal$\beta$1-3[Fuc$\alpha$1-4]GlcNAc$\beta$1-4[Fuc$\alpha$1-3]GlcNAc$\beta$1-3Gal$\beta$1-4Glc, said antibody having a detectable label; and
detecting the presence of said label in a breast or breast-associated lymphoid tissue of said host;
wherein the presence of said label in a breast or breast-associated lymphoid tissue is indicative of the presence of breast carcinoma in said host.

21. A method according to claim 20, wherein said antibody is a monoclonal antibody.

22. A method according to claim 21, wherein said monoclonal antibody is IgM monoclonal antibody designated 43-9F secreted by hybridoma cell line having a deposit number ECACC 85013101 or an antibody which specifically binds the epitope specifically bound by the monoclonal antibody designated 43-9F.

23. A method according to claim 20, wherein said label is a radionuclide.

24. A method for evaluating the risk of breast carcinoma relapse in a human host after the removal of a breast carcinoma tumor from said host, said method comprising the steps of:
combining a sample from said human host with monoclonal antibodies which specifically bind the carbohydrate Gal$\beta$1-3[Fuc$\alpha$1-4]GlcNAc$\beta$1-4[Fuc$\alpha$1-3]GlcNAc$\beta$1-3Gal$\beta$1-4Glc; and
detecting the amount of immune complexes;
wherein, the presence of said immune complexes in indicative of the risk of breast carcinoma relapse of said host.

25. A method according to claim 24, wherein said monoclonal antibody is IgM monoclonal antibody designated 43-9F secreted by hybridoma cell line having deposit number ECACC 85013101 or an antibody which specifically binds the epitope specifically bound by the monoclonal antibody designated 43-9F.

26. A method according to claim 24, wherein said sample is tissue.

27. A method according to claim 24, wherein said sample is a blood-derived sample.

28. A method according to claim 24, wherein said monoclonal antibodies are labeled with a detectable label.

29. A method according to claim 24, wherein said detecting is achieved by detection of binding of a labeled antibody having binding specificity for said monoclonal antibody.

* * * * *